US010827941B2

(12) United States Patent
Duckert et al.

(10) Patent No.: US 10,827,941 B2
(45) Date of Patent: Nov. 10, 2020

(54) SYSTEM AND METHODS FOR QUALIFICATION OF ECG DATA FOR REMOTE ANALYSIS

(71) Applicant: General Electric Company, Schenectady, NY (US)

(72) Inventors: David Wayne Duckert, Wauwatosa, WI (US); Chiranjiv Singh, Wauwatosa, WI (US); Brian J. Young, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 156 days.

(21) Appl. No.: 15/833,131

(22) Filed: Dec. 6, 2017

(65) Prior Publication Data

US 2019/0167141 A1   Jun. 6, 2019

(51) Int. Cl.
*A61B 5/00* (2006.01)
*A61B 5/0468* (2006.01)
*A61B 5/04* (2006.01)

(52) U.S. Cl.
CPC .......... *A61B 5/0468* (2013.01); *A61B 5/0006* (2013.01); *A61B 5/0022* (2013.01); *A61B 5/04017* (2013.01)

(58) Field of Classification Search
CPC . A61B 5/0006; A61B 5/0022; A61B 5/04017; A61B 5/0468; G16H 40/67
See application file for complete search history.

(56) References Cited

U.S. PATENT DOCUMENTS

| 9,254,092 B2 | 2/2016 | Albert et al. | |
| 2002/0026292 A1* | 2/2002 | Isami | G16H 40/67 702/188 |
| 2012/0123891 A1* | 5/2012 | Patel | G06Q 30/0605 705/26.2 |
| 2014/0276162 A1* | 9/2014 | Albert | A61B 5/04012 600/523 |

* cited by examiner

*Primary Examiner* — George Manuel
(74) *Attorney, Agent, or Firm* — Andrus Intellectual Property Law, LLP

(57) ABSTRACT

A method of obtaining and analyzing ECG data from a patient or group of patients is disclosed. The ECG data is obtained from the patient at an acquisition device. Once the ECG data is obtained, the ECG data is transmitted to an analysis server that is operated by an analysis provider and is located remote from the location of the acquisition device. Along with the ECG data, acquisition parameters are transmitted to the analysis server. At the analysis server, one of a plurality of algorithms is selected to analyze the ECG data. If an abnormality is detected, the patient information is directed to a healthcare provider who can then contact the patient to schedule an appointment. Based upon the referral, a referral fee can be transferred from the healthcare provider to the analysis provider. The patient can be prompted to provide additional information and selections that dictate the level of analysis generated.

16 Claims, 5 Drawing Sheets

SYSTEM AND METHODS FOR QUALIFICATION OF ECG DATA FOR REMOTE ANALYSIS

BACKGROUND

The present disclosure relates to a method and system for analyzing ECG data from patients. More specifically, the present disclosure relates to a system and method that receives ECG information from patients and provides analysis techniques that utilize remote analysis and data reporting.

Cloud-based technology is modifying and changing the ways that software services are being sold and utilized. Currently, instead of owning a copy of a software product, cloud-based computing allows users to access software programs utilizing cloud-base technology and pay only for what the user utilizes. Cloud-based computing allows large applications that consume significant amounts of storage space to be stored at remote locations and be accessed by a user utilizing an online browser. Cloud-based computing creates many advantages for the user and enables different types of business models.

Presently, many different companies and manufacturers sell electrocardiographs that include both the physical hardware to capture an ECG from a patient and the software algorithms required to identify arrhythmias and other irregularities in the ECG data. Such electrocardiographs must have the required processing power and storage space to analyze the ECG data and provide diagnostic information to a clinician or user. The electrocardiographs are typically updated when new processing algorithms are developed, which may require additional storage space on the electrocardiograph machine.

SUMMARY

The systems, devices and methods described herein relate to processing and analyzing of medical data, and in particular, analyzing and processing ECG data obtained from patients. In accordance with one embodiment of the disclosure, ECG data is obtained from one or more patients at an acquisition device that is located at a first location. The acquisition device can be one of a wide variety of different types of hardware equipment, including exercise machines, automobile steering wheels, personal health tracking wearable devices, watches, smartphones, dedicated kiosks or any other type of device that is able to obtain ECG data from a patient and digitize the ECG data.

Once the ECG data is obtained from the patient, the ECG data is transmitted to an analysis server that is operated by an analysis provider and is positioned at a second location that is remote from the acquisition device. The analysis server includes a plurality of algorithms, each of which is operable to detect abnormalities in the ECG data.

In addition to transmitting ECG data to the analysis server, the method also transmits acquisition parameters that are related to the specific acquisition device and conditions present when the ECG data is obtained from the patient. The acquisition parameters can include the specific parameters related to the acquisition device or could be identification information that is used by the analysis server to lookup specific parameters related to the acquisition device. In each case, the analysis server is able to determine acquisition parameters that can be used to select the specific algorithm used to process the ECG data.

Once the ECG data and acquisition parameters are obtained, the selected algorithm operating on the analysis server detects abnormalities present in the ECG data. If no abnormalities are detected, the patient is informed of the "normal" ECG data. However, if abnormalities are detected, the patient is referred to a healthcare provider, which may be a medical clinic, healthcare facility, or physician. Specifically, patient information, the analysis results from the analysis server and the ECG data are sent to a subscribing healthcare provider. Upon receipt of this information, the healthcare provider contacts the patient to schedule an appointment with the healthcare provider. The scheduling of the additional appointment is thus driven by the analysis of the ECG data and the detected abnormalities. In this manner, the healthcare provider contacts patients that are in need of further attention, which will lead to a high rate of billable appointments. Since the referral increases the revenue generated by the healthcare provider, a referral fee is directed from the healthcare provider to the analysis provider that operates the analysis server.

In another embodiment of the present disclosure, a microsite can be created within a healthcare provider's health website to provide a portal for access by a patient. The microsite portal allows the patient to upload ECG data to the health website. Once the ECG data is obtained by the health website, the ECG data is transmitted to the analysis server for processing. If abnormalities are detected, the healthcare provider that operates the health website contacts the patient to schedule additional appointments. Once again, the additional appointments based on the analysis of the ECG data generate additional revenue for the healthcare provider a referral fee can be transmitted from the healthcare provider to the analysis provider to compensate for the additional revenue created by the analysis server.

In yet another embodiment of the present disclosure, the analysis provider and an interested entity, such as a healthcare provider, government agency or insurer can work together to identify a segment of a patient population having an overall cardiac health that could be improved or having a cost of future treatment that could be reduced by utilizing early ECG analysis. Once the patient population is identified, the patients in the patient population are contacted and urged to obtain an ECG reading. The ECG reading can be carried out by one of the acquisition devices and the obtained ECG data transmitted to the analysis server. If abnormalities are detected, the patient is contacted by the healthcare provider to schedule additional appointments. The early detection of healthcare related issues through the increase in the number of ECG measurements has a cost benefit that can be calculated by the analysis provider. Since healthcare costs are reduced, the analysis provider obtains payment based upon the amount of healthcare savings.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION

Figure 1:
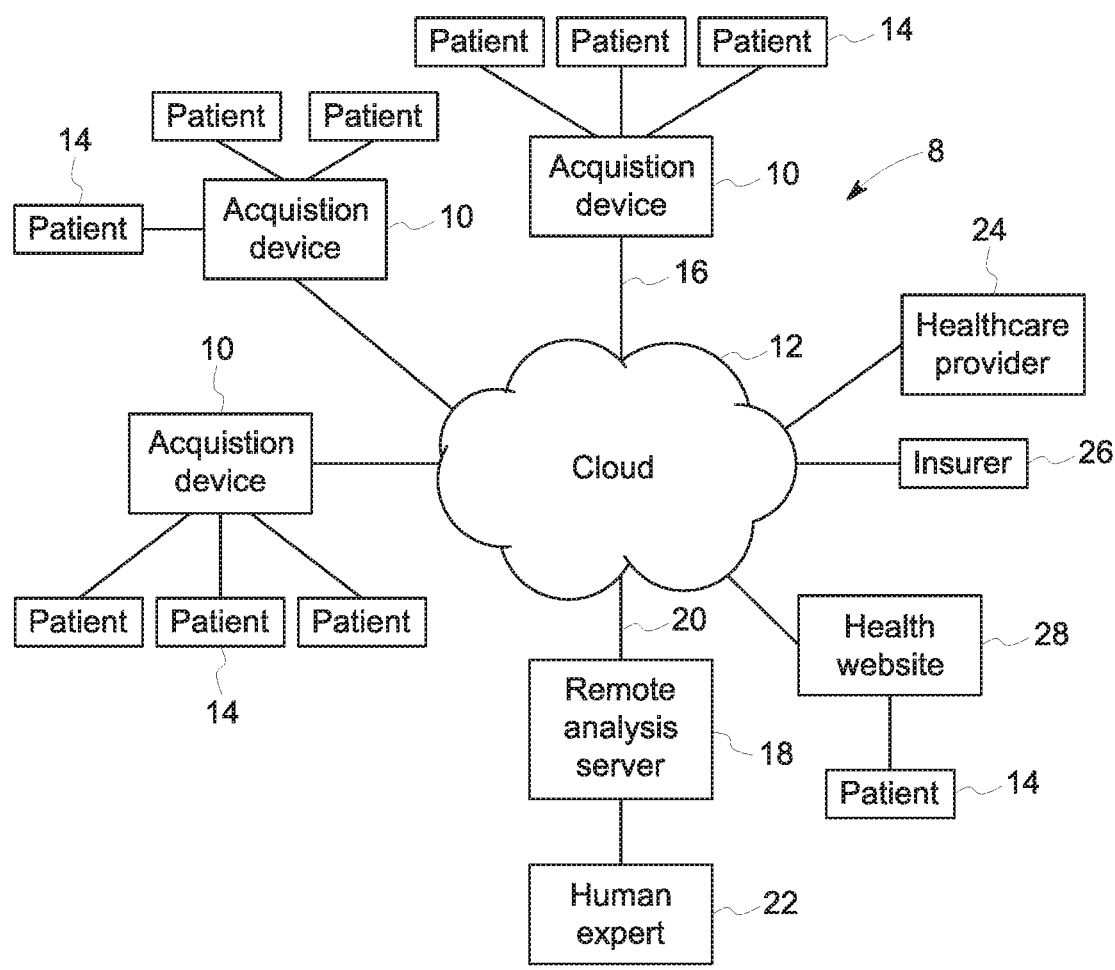
FIG. 1 is a schematic illustration showing the communication between various acquisition devices and remote servers, healthcare providers and insurers utilizing cloud-based communication.

FIG. 1 illustrates a general communication system 8 that enables the methods and systems of the present disclosure. In the embodiment shown in FIG. 1, a plurality of different types of ECG acquisition devices 10 are shown communicating information to remote locations through the internet, which is referred to as the "cloud" in FIG. 1 and throughout the present disclosure. The ECG acquisition devices 10 each function to obtain ECG data from one or more patients 14. Although the embodiment shown in FIG. 1 is described as obtaining ECG data from the patients 14 utilizing the ECG acquisition devices 10, it should be understood that the acquisition devices 10 could obtain other types of medical data from the patient, such as blood pressure, weight, heart rate, temperature, or any other type of medical data that may be useful in analyzing the current health status of the patient 14.

In the embodiment shown in FIG. 1, the ECG acquisition device can be one of a large variety of hardware devices that are able to record ECG information from a patient. These devices could be traditional ECG recording devices, ambulatory ECG recording devices such as a Holter monitor or an event recorder. Further, current hardware devices exist that incorporate ECG sensing electrodes into other types of devices such as exercise machines, automobile steering wheels, watches, smartphones or any other contemplated type of location or device where the interaction between the patient 14 and the acquisition device may be sufficient to obtain ECG information from the patient.

In other embodiments, the acquisition devices could be stand alone ECG acquisition devices that are located in public areas, such as shopping malls, office buildings, health clinics, or any other place where a patient could interact with the acquisition device 10 to obtain ECG information from the patient. As an example, a kiosk could be created that includes two metal disks on the kiosk which instructs the patient to touch the metal disks to obtain the ECG information. The kiosk-based acquisition device would contain the necessary hardware to digitize the ECG information obtained from the user and either provide a digital copy to the patient or transmit the obtained ECG data through the cloud 12. The communication between the acquisition device 10 and the cloud could be through a Wi-Fi network, direction connection to the internet, a mobile data network, a cellular network, direct connection to phone lines or any other type of communication that would allow the communication line 16 between the acquisition device 10 and the cloud 12 to exist.

In addition to obtaining the ECG information at the acquisition device 10, it is contemplated that he acquisition device 10 may allow the patient to input data regarding their healthcare provider, insurance provider, and their condition or status at the time the ECG is taken. This additional information would be associated with the ECG data and transmitted over the cloud 12. As an example, the patient can input symptoms felt before and/or during the ECG recording and can input activities the user was engaged in prior to and/or during the ECG recording process.

Since the ECG acquisition devices 10 are contemplated as taking multiple different forms and/or configurations, it is important for the method and system of the present disclosure to communicate various acquisition parameters that are associated with the acquisition device 10 and communicate this information with the patient specific ECG data being transmitted over the cloud 12. One method of associating the required acquisition parameters with the ECG data would be to pre-register each of the data acquisition devices 10 such that the acquisition device 10 would be associated with ECG data when the data is transmitted over the cloud. Such a registration service would allow for identification data of the acquisition device 10 to be transmitted with the ECG data from the patient such that during subsequent review and analysis at the server 18, the acquisition device parameters would be known to the analysis server 18.

In accordance with a second alternate embodiment, the relevant acquisition parameters that are associated with the acquisition device 10 could be transmitted along with the ECG data. Thus, instead of requiring the acquisition device 10 to be pre-registered, the ECG data transmitted would include the specific acquisition parameters such that the acquisition parameters would be incorporated and utilized during the analysis of the patient ECG data. It is contemplated that this second, alternate embodiment would require additional data to be transmitted with each set of ECG data. However, the method would eliminate the need for pre-registration of each of the acquisition devices, which may provide additional benefits.

Since a large variety of currently available and yet to be developed acquisition devices 10 are contemplated, it is important that the acquisition parameters be known during the analysis of the ECG data. As an example, ECG data that is received from the patient can be used for different clinical purposes, such as rhythm interpretation, interpretation of conduction and ischemic conditions, and interpretation of contour based features. Depending upon the clinical use of the ECG data, specific aspects and parameters of the acquisition device 10 and the resulting ECG data from the patient are relevant. Such acquisition parameters can include sample rate, frequency response, number and placement of the ECG leads, pacemaker detection, and data resolution. By either pre-registering the acquisition device 10 or by sending the acquisition parameters along with ECG data, the analysis of the ECG data from the patient can be properly analyzed.

In the embodiment shown in FIG. 1, the ECG data obtained from each of the patients 14 by the acquisition device 10 is transmitted along the communication line 16 to the cloud 12. A remote analysis server 18 is shown in FIG. 1 as also communicating to the cloud 12 over communication line 20. The remote analysis server 18 is contemplated as being operated and provided by an analysis provider that either houses or maintains the server 18. The analysis provider can be any type of entity that is able to provide a remote server 18 that receives ECG data and analyzes the ECG data for irregularities in the ECG data, which can include a variety of different diagnoses, including arrhythmia. The remote analysis server 18 will include a number of algorithms that are able to analyze the ECG data obtained from the patient and provide automated analysis. These algorithms are known and used in many stand alone electrocardiograph machines and systems, such as provided by GE Healthcare and others. In the embodiment shown in FIG. 1, a human expert 22 can communicate with the remote analysis server 18 to provide human over-reading of the ECG data if necessary, as will be discussed in greater detail below. The human expert 22 could comminute directly with the server 18 or could communicate to the server 18 over the cloud 12.

It is contemplated that the remote analysis server would be operated and controlled by an analysis provider, which could include current companies that manufacture and provide electrocardiograph hardware. However, it is also contemplated that the analysis provider that operates and controls the remote analysis server 18 could be any other type of company or entity that develops analysis algorithms and provides the required hardware to function as the remote analysis server. It is contemplated that the remote analysis server would include the required computing processor or processors to receive ECG data from a large number of patients and analyze the data in a timely manner to return analysis information in a time frame as desired.

In currently available systems in which the electrocardiograph receives information directly from the patient and the algorithms are carried out within the electrocardiograph, the data acquisition parameters are not a problem since they are known to the algorithm operating on the electrocardiograph. However, in the embodiment shown in FIG. 1 in which the remote analysis server is located remote from the various acquisition devices 10, the source and acquisition parameters associated with the ECG is important. Thus, there must be system and method in place such that the ECG data can be qualified in terms of the acquisition parameters so that the analysis algorithms operating on the remote analysis server 18 and the results generated can be returned that are clinically appropriate for both their intended use and based upon the data acquisition parameters. As an example, if one of the acquisition devices includes electrodes that provide 12-lead ECG data, the remote analysis server 18 must be able to identify this type of data and utilize an algorithm that is intended for the analysis of 12-lead ECG. Likewise, if the data is not acquired from standard lead positions or if the data acquisition device is of such configuration that it has lower bandwidth, the interpretation carried out by the remote analysis server 18 must utilize an appropriate algorithm. As indicated above, the data acquisition device 10 can either be pre-registered or can communicate acquisition parameters along with the patient ECG data. The data acquisition parameters are typically published or available for each of the data acquisition devices 10 and can thus be accessed by the remote analysis server 18 prior to selecting the appropriate analysis algorithm.

In accordance with the embodiment shown in FIG. 1, the remote analysis server 18 will receive ECG data from one of the acquisition devices 10 along with either device identification information or information related to the acquisition parameters. If the information includes the identification of the acquisition device, the remote analysis server 18 will utilize some type of look up table to obtain the acquisition parameters related to the acquisition device. Such look up table would include published information related to the acquisition device, which is typically available from the device manufacturer. Once the acquisition parameters are obtained, the remote analysis server 18 can select and run the required algorithm based upon the acquisition parameters.

In accordance with another embodiment in which the acquisition parameters are transmitted along with the ECG data, the remote analysis server 18 would interpret the acquisition parameters and select and utilize the required analysis algorithm based upon the acquisition parameters. In each case, the remote analysis server 18 utilizes different algorithms based upon the acquisition parameters obtained from the acquisition device 10. In this manner, the remote analysis server 18 can tailor the analysis and selected algorithm based upon the type of acquisition device 10 utilized to obtain the ECG data from the patient 14. Such identification allows for a wide variety of different acquisition devices 10 to be utilized such that the ECG data analysis is able to be performed independent of the type of acquisition device 10.

In the embodiment shown in FIG. 1, the remote analysis server 18 and the acquisition devices 10 each communicate with each other through the cloud 12. In addition, various other entities, such as a healthcare provider 24, an insurer 26, and a health website 28 also from part of the overall system 8. Each of these separate entities can communicate with the remote analysis server 18 utilizing the cloud 12. The health website 28 may be one of a wide variety of health-based websites that allow an individual patient or user 14 to access information. As an example, the health website 28 could be WebMD, Mayo Clinic, Cleveland Clinic, or any other type of large website controlled and operated by healthcare providers or facilities that provides patients access to information.

Figure 2:
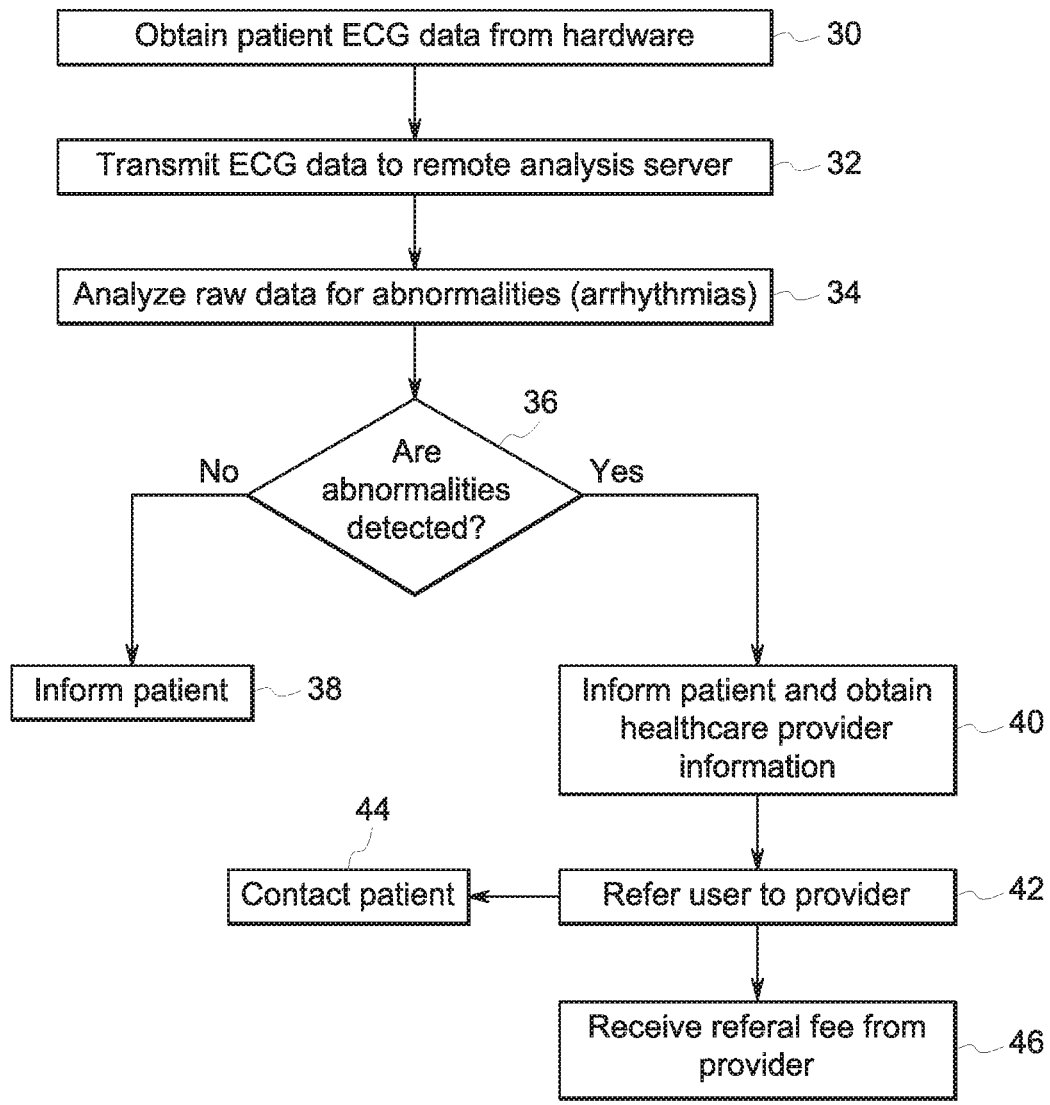
FIG. 2 is a flow chart illustrating one method in accordance with an embodiment of the present disclosure.

The system and configuration shown in FIG. 1 allows for a wide variety of different types of business models to be carried out generally based upon the remote analysis of ECG data from the large and wide variety of different types of ECG data acquisition devices 10. A first method made possible by the system of FIG. 1 is illustrated in FIG. 2. The method of FIG. 2 will be explained in detail below with reference to the system 8 shown in FIG. 1.

In step 30, the ECG acquisition device 10 obtains patient ECG data from the patient in the manner described above. As indicated above, the acquisition device 10 used to obtain information from the patient 14 can be one of a wide variety of hardware devices, such as an exercise machine, an automobile steering wheel, an electrocardiograph, a kiosk, a watch, a fitness tracker, smart phone or a wide variety of other hardware devices. This ECG data obtained from the individual patient is digitized and transmitted to the remote analysis server 18 as illustrated in step 32. The transmission of the digitized ECG data to the remote analysis server can be carried out over the cloud 12 utilizing a wide variety of communication techniques to create the communication line 16. As an example, the communication line 16 between the acquisition device 10 and the cloud 12 may be a cell phone communicating over either a cellular data network or utilizing Wi-Fi. In addition, the ECG acquisition device 10 could communicate directly to the remote analysis server 18 over to the cloud utilizing communication controlled by the acquisition device 10. In one contemplated embodiment, a kiosk in a mall could include two metal disks that allow the patient to place their hands on the metal disks such that the kiosk would obtain the required ECG data. Once the data is obtained, the kiosk that forms the acquisition device 10 would utilize required hardware at the kiosk lever to digitize the ECG data and send the digitized ECG data over the cloud 12.

It is contemplated that the ECG data transmitted by the data acquisition device over the cloud may or may not include patient data. If the results from the remote analysis server 18 are going to be presented to the patient immediately at the acquisition device, patient identification information may not needed. Instead, the patient may only need to provide relevant information such as age, height, weight, and other parameters that may be utilized in carrying out the analysis utilizing the algorithms present at the remote analysis servers. However, in embodiments in which the information obtained from the patient is used in further analysis, patient identification information will be obtained. This patient identification information may include unique identifiers to the patient, such as a social security number, cell phone number, health insurance account number, healthcare provider information, or any other information that can be utilized in subsequent processing to inform the patient of the analysis results.

Referring back to FIG. 2, once the ECG data and acquisition parameter related to the acquisition device 10 are transmitted to the remote analysis server 18, the remote analysis server selects the most appropriate analysis algorithm and utilizes the selected algorithm to analyze the raw ECG data for abnormalities, as illustrated in step 34. These abnormalities may be any type of abnormality identified in an ECG. In the embodiment illustrated in FIG. 2, these abnormalities are focused on arrhythmias present in the ECG data.

In step 36, if no abnormalities are detected, such positive analysis is transmitted back to the acquisition device 10 from the remote analysis server. This information could be presented immediately to the patient as illustrated in step 38. Alternatively, if the processing carried out the remote analysis server 18 will take more time than is available for the patient to remain at the acquisition device 10, the patient 14 may be prompted to provide contact information, such as a cell phone number. If the ECG is determined to be normal in step 36, the patient would be notified as soon as possible that the ECG analysis returned a "normal" analysis result. In the embodiment shown in FIG. 2, it is contemplated that the patient would be charged a nominal fee for the analysis of the ECG data and the return of the "normal" determination. The analysis result returned to the patient in step 38, if provided on the cell phone, would utilize the cell phone or smartphone as the graphic user interface (GUI) to return the analysis results. These results could include analysis information, depictions of ECG graphs, or any other information that could be presented on the GUI of the patient's cell phone.

If abnormalities are detected in the ECG data in step 36, the method moves to step 40 in which the patient is informed of the possible presence of an arrhythmia or abnormality in the ECG data. The patient can be notified in the same manner as in step 38, namely either at the acquisition device 10 or through a cell phone or computer address provided by the patient during the initial acquisition phase. In step 40, the method also obtains healthcare provider information from the patient. As indicated above, the healthcare provider information could be obtained when the patient initially begins the ECG acquisition process. Alternatively, if an abnormality or irregularity is identified, the method could contact the patient utilizing either the email address or cell phone.

The healthcare provider information obtained from the patient in step 40 identifies the current healthcare provider for the patient. This may be a clinic, hospital, healthcare group, or any other type of healthcare provider information that is available from the patient. The patient may be also asked to provide insurance information, which would be used to select a healthcare provider if the patient does not have a current healthcare provider and would need assistance in selecting a healthcare provider.

Once the healthcare information is obtained from the patient in step 40, the method moves to step 42 in which the remote analysis server operated by the analysis provider makes a direct referral of the patient to a healthcare provider network, insurer, or a specific physician. The referral generated by the analysis provider is based directly upon the identification of an abnormality in an ECG analyzed by the remote analysis server. The referral generated in step 42 would include as much information about the patient as is available, including patient identification information, the raw ECG data obtained from the patient, and an automated arrhythmia analysis report that is created by the remote analysis server 18. This information would be the information necessary for the healthcare provider to obtain initial information about the patient and would allow the provider to contact the patient directly in step 44 to set up an appointment, which would generate additional fees for the healthcare provider. The referral from the analysis provider operating the remote analysis server 18 will generate additional revenue for the healthcare provider, insurer, or physician utilizing the referral in step 44.

As can be understood in FIG. 1, the wide variety of different acquisition devices 10 and non-typical locations for the devices allow for a greater population of patients 14 to be serviced at the non-typical locations, such as shopping malls, on exercise equipment or any other location in which ECG data can be obtained from non-typical sources outside of a typical electro-cardiograph. As an added benefit, many patients will have ECG data recorded when the patient is otherwise healthy simply based on the ease of access. The additional number of patients 14 that will have ECG data analyzed with aid in preventing high-risk, high-costs medical events by detecting arrhythmias earlier and before a catastrophic event may occur.

In the method shown in FIG. 2, the last step in the process is for a referral fee to be directed from the healthcare provider to the analysis provider as shown in step 46. This referral fee is a direct result of a patient having an arrhythmia/abnormality detected in ECG data being referred to the healthcare provider, which generates additional revenue for the healthcare provider. The referral fee can be utilized along with any charge to the patient to fund and operate the remote analysis server 18 by the analysis provider. As can be understood by the above description, the use of ECG data obtained from patients at non-typical locations will aid in early detection of health problems, which will increase the overall population health and decrease costs associated with higher acuity healthcare services.

Figure 3:
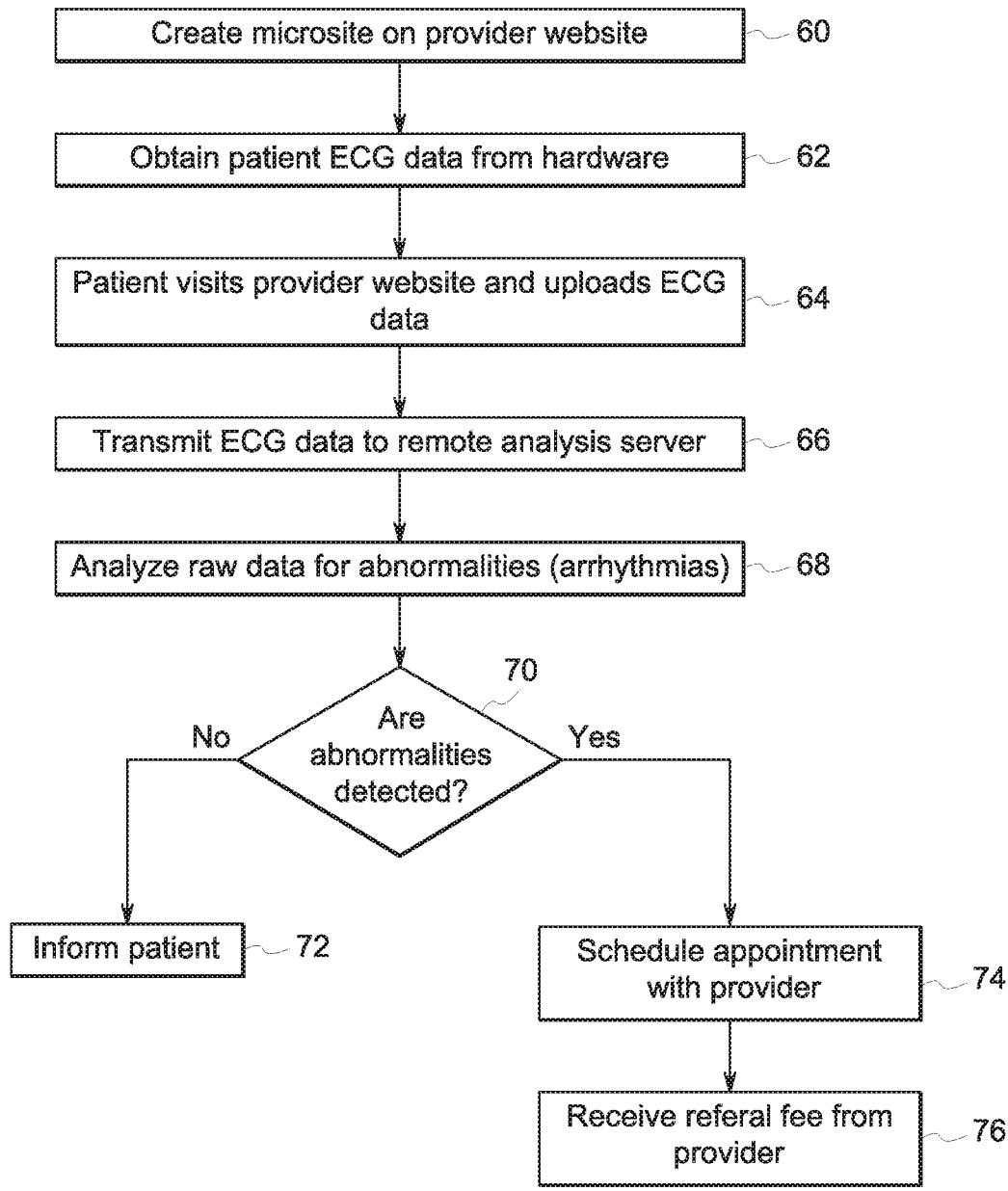
FIG. 3 is a flow chart illustrating a second method in accordance with another embodiment of the present disclosure.

FIG. 3 illustrates another method that can be carried out utilizing the system configuration generally shown in FIG. 1. The method carried out in FIG. 3 is similar to the method of FIG. 2. However, the embodiment shown in FIG. 3 utilized an entry point that is incorporated into the health website 28 shown in FIG. 1. Referring now to FIG. 3, in step 60 a "microsite" is developed by the analysis provider and is incorporated into the health website 28. The "microsite" incorporated into the website provides an access point for the patient 14 to upload or input ECG data and other patient information. In step 62, the patient is directed to input ECG information into the microsite. The ECG information can be stored data that is obtained from any one of the ECG acquisition devices 10. As discussed previously, the acquisition devices can be watches, phones, exercise equipment, kiosks or any other type of acquisition device that is able to obtain ECG data from the patient. The ECG data can be stored at some location directed by the patient or can be directly into the microsite created on the health website 28. Once the patient has the ECG data from one of the acquisition devices, the patient visits the health website 28 and is prompted to upload ECG data into the website. The health website is a typical website provided by healthcare providers, such as Mayo.com, WebMD, or other healthcare providers that operate health websites 28 for the benefit of their plan participants or patients.

Once the patient visits the provider website and uploads the ECG data in step 64, the ECG data is transmitted to the remote analysis server as illustrated in step 66. As discussed above in the description of FIG. 2, once the ECG data is transmitted to the remote analysis server, the remote analysis server selects and utilizes one of a series of algorithms to analyze the ECG data to determine whether abnormalities are present in the ECG data as indicated in steps 68 and 70. If no abnormalities are detected, the patient is advised in the same manner as discussed with respect to step 38. However, if abnormalities are detected, since the patient is already accessing a provider health website 28, the patient is directed to schedule an appointment with the provider as indicated in step 74. Unlike the embodiment shown in FIG. 2, information about the patient does not need to be provided to the healthcare provider since the patient is already accessing the microsite created by the analysis provider within the health website 28 operated by the healthcare provider. It is contemplated that the appointment scheduled with the provider in step 74 can be accomplished immediately online within the healthcare provider's health website 28. Since the microsite can be created by the analysis provider, the analysis generated by remote analysis server 18 again identifies patients that may not have otherwise known there were abnormalities present in ECG information. The increase in number of patients will increase the revenue to the healthcare provider and the analysis provider will again receive a referral fee as indicated in step 76. The method shown in FIG. 3 closely corresponds to the method of FIG. 2 but instead utilizes a microsite created by the analysis provider on the healthcare provider's website 28 to both provide additional features to the clients/patients of the healthcare provider and also to identify additional patients that may need to schedule an appointment with the healthcare provider.

Figure 4:
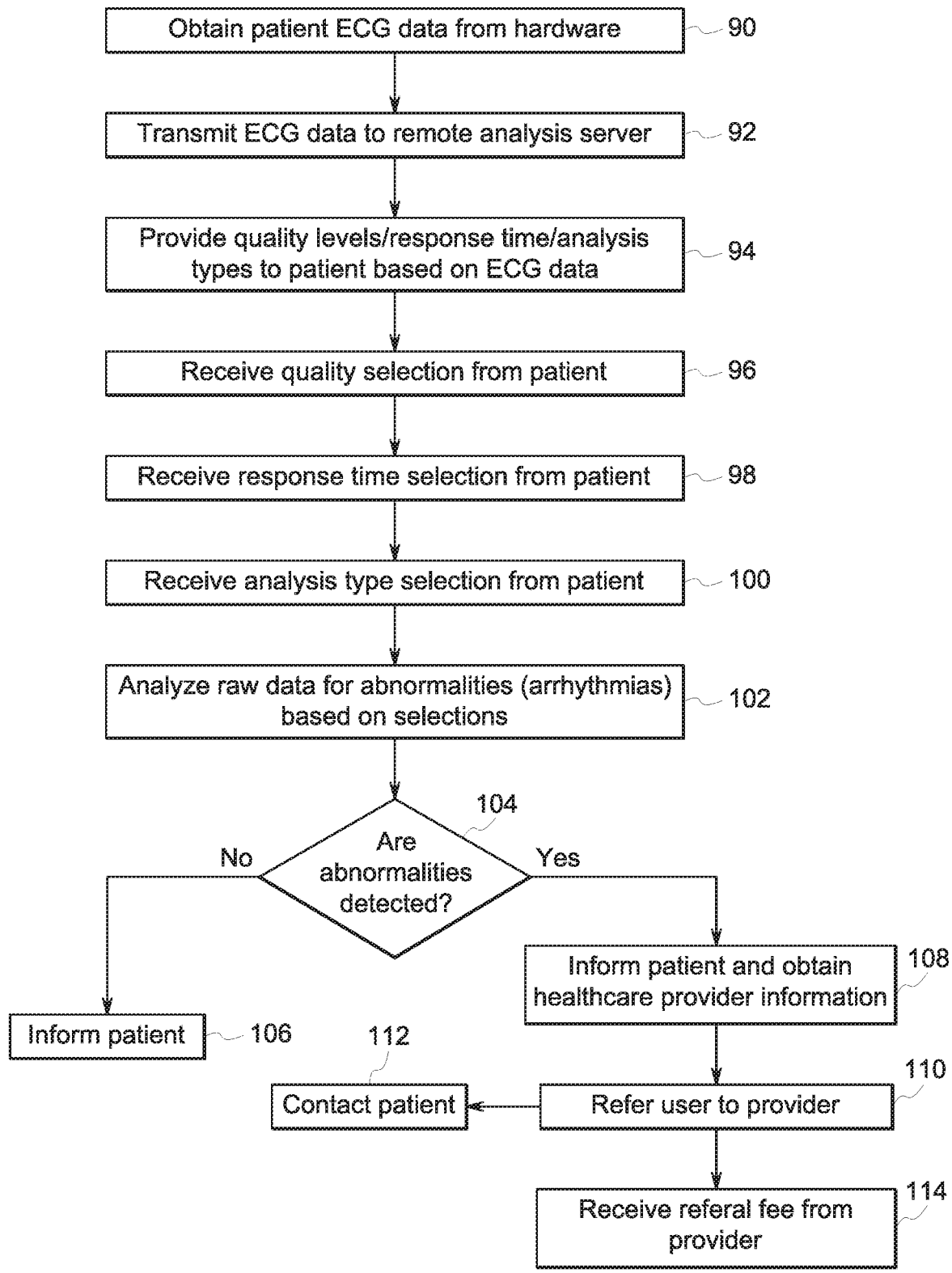
FIG. 4 is a flow chart illustrating a third method in accordance with another embodiment of the present disclosure.

FIG. 4 illustrates yet another method that can be performed and carried out utilizing the configuration and system 8 shown in FIG. 1. Like the embodiments shown in FIGS. 2 and 3, the method of FIG. 4 obtains ECG data from the various different types of hardware devices as illustrated in step 90. The ECG data obtained from the patient is transmitted to the remote analysis server 18 as illustrated in step 92. However, in the method shown in FIG. 4, once the ECG data is uploaded to the remote analysis server 18, the patient is prompted to provide additional information and selections as to the type, cost and speed of analysis to be provided by the remote analysis server. The information obtained from the patient in step 94 will be presented to the patient along with information as to the price points associated with each of the selections.

In step 96, the remote analysis server 18 initially inquires with the patient as to the quality level of review that is desired. The quality level review may span from the basic arrhythmia analysis that can be automatically performed by the algorithms contained on the remote analysis server 18 to human over-read analysis to longitudinal analysis. Typically, the human over-read and longitudinal analysis requires a significant amount of additional attention and thus will not only increase the quality level of the determination but will also increase the total price point to the patient.

When the remote analysis server initially receives the ECG data from the patient, an initial algorithm at the remote analysis server with inspect the ECG data to determine the quality level of the ECG data. This quality level will take into account the length of the ECG recording, the amount of noise present in the ECG data, the number of leads used to obtain the data and the type of acquisition device that was used to obtain the data. As discussed previously, the different types of acquisition devices can vary greatly and thus will determine the type of analysis that can be performed by the remote analysis server 18.

If the patient selects a human over-read in step 96, the remote analysis server 18 then carries out the step of contacting a human clinician to over-read the analysis generated by the algorithms operating on the remote analysis server. The specific nature of the human over-read can also be selected by the patient. The different types of human over-read include an auction approach, standard human over-read, premium over-read by a noted specialist or marquee provided (e.g. Cleveland Clinic). Each of these different levels of human over-read may have a different price point associated with the analysis. All of these different options are presented to the patient and the patient is able to select between the different types of human over-read depending upon the type of analysis and cost desired by the patient. FIG. 1 indicates that the human expert 22 can access the ECG data from the remote analysis server 18 directly or possibly through the cloud 12.

Once the patient has provided the quality selection in step 96, the method moves to step 98 in which the patient is asked to select the desired response time for the analysis. A response time can vary between minutes, hours or days. Typically, the faster the response time, the higher the price point. As an example, if the user would like a premium human over-read returned in hours, the price point may be dramatically higher than an automated algorithm analysis returned in a matter of days. Once again, step 98 allows the patient to select the response time and pay accordingly.

In step 98, if a user uploads ECGs in bulk the user could specify rules for priority such that if a dangerous arrhythmia is detected, an immediate response should be generated and an immediate human over-read should be ordered. Again, this step allows the patient/user to dictate the cost of analysis by selecting the quality of the review and the response time.

In step 100 the patient is able to specify the type of analysis desired, such as standing resting analysis, holter analysis, stress tests, heart rate recovery. Each type of analysis is presented at varied price points. By allowing the patient to select the type of analysis, the system again can offer the patient a variety of options at different price points.

The analysis type selected by the patient in step 100 could also be carried out by the remote analysis server 18 upon receiving the uploaded patient ECG file. The remote analysis server 18 can review the uploaded ECG data and automatically suggest the appropriate type of analysis depending upon the type of acquisition device and other information related and present in the obtained ECG information.

Once the user has made the selections in steps 96, 98 and 100, the method moves to step 102 and carries out the required analysis based upon the patient selections. In step 104, the method determines whether abnormalities are detected and if no abnormalities are detected, the patient is informed as shown in step 106. However, like the method discussed in FIG. 2, if abnormalities are detected, the patient is informed in step 108 and the analysis is provided to the healthcare provider as part of the referral in step 110. The provider then contacts the patient in step 112 and a referral fee is paid to the analysis provider in step 114.

Since the method in FIG. 4 requires additional patient input, it is contemplated that such communication with the patient would occur through some type of website or dedicated input terminal. Since there is additional patient input, it is contemplated that the method of FIG. 4 will provide additional functionality such as possibly reminding the patient to capture additional ECG data in the future. Such reminders can be in the form of email, automated telephone calls, automated texts or other means. In addition, it is contemplated that the patient can choose to store a longitudinal patient record in a secure and HIPAA compliant cloud server through feature analysis and/or comparison to subsequent ECG data obtained utilizing the acquisition devices. In this manner, additional patient options are presented and the cloud server time is optimized based upon specific instructions from the patient as to the level of service and price points desired.

Figure 5:
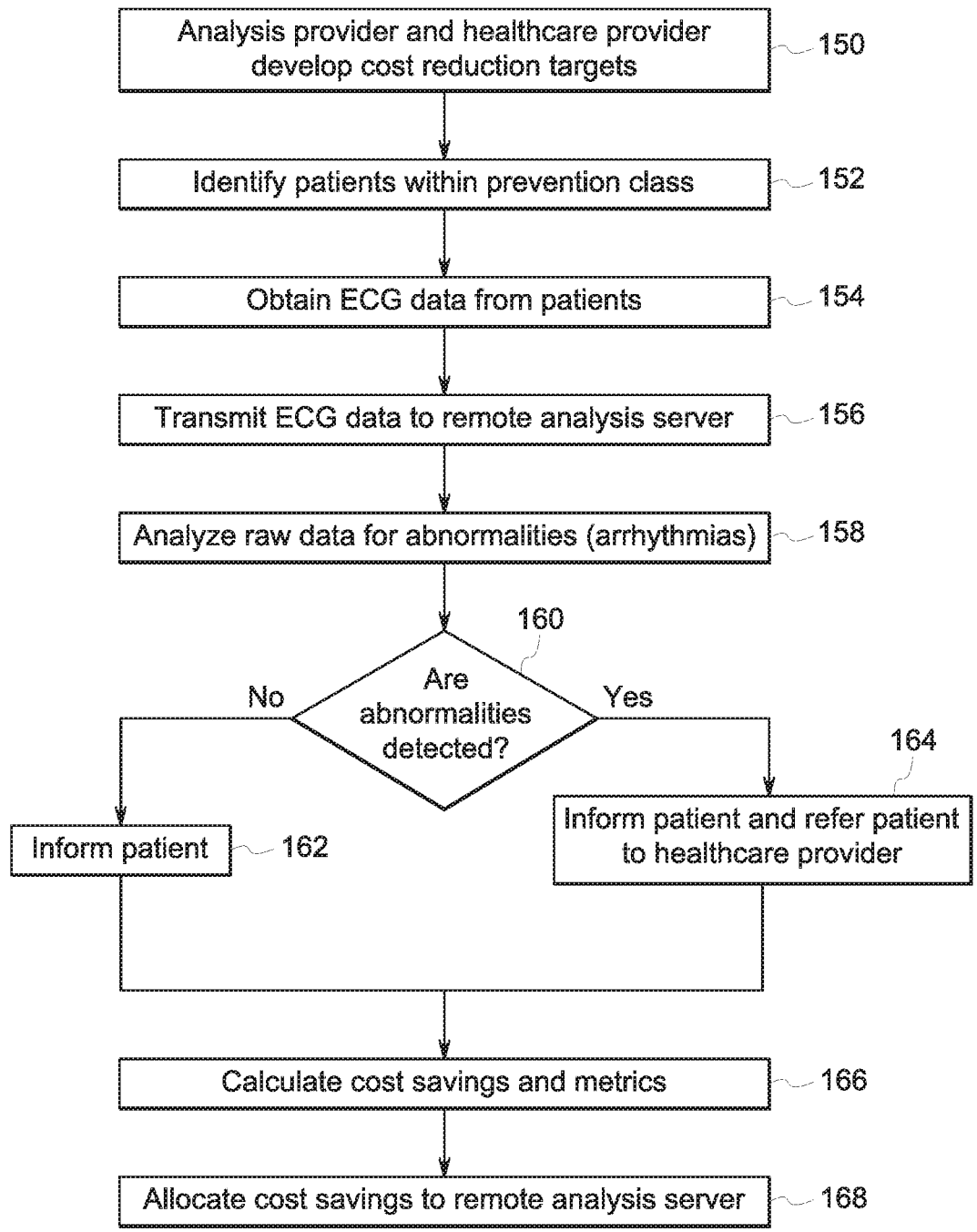
FIG. 5 is a flow chart illustrating a fourth method in accordance with another embodiment of the present disclosure.

Referring now to FIG. 5, there shown is yet another method that can be carried out utilizing the system configuration shown in FIG. 1. In the embodiment shown in FIG. 5, the method provides a comprehensive solution for cardiac health, including hardware, cloud services for arrhythmia analysis and population metrics. The focus of the method shown in FIG. 5 is to improve the overall cardiac health of a population of patients or to reduce the overall cardiology related expenses of a population of patients. The method of FIG. 5 utilizes the availability of the ECG acquisition devices 10 and the transmission of ECG data from the individual patients to a remote analysis server in an attempt to improve the health of a group of patients and/or to reduce the healthcare related expenses of this population of patients.

In the method of FIG. 5, the analysis provider that operates the remote analysis server 18 contracts with some other entity, such as a healthcare provider, government agency, insurer or other entity that has a goal of cost reduction. After contracting with the external agency, cost reduction targets are calculated based upon projections made using a cost benefit analysis of both early detection and intervention. As an example, one target may be to identify numbers of an elderly population that have AFIB. By identifying these members of a population and providing increased monitoring and analysis, intervention or treatment may be available to avoid a more costly event, such as a stroke. Performance metrics can be established between the analysis provider and the entity to share in the potential savings and positive outcomes. The analysis provider will receive financial incentives based upon when outcomes are met and thus has a direct stake in the improved healthcare of the group of patients.

As illustrated in FIG. 5, the healthcare provider, which may be a government agency, insurer or healthcare clinic, meets with the analysis provider to develop cost reduction targets, as illustrated in step 150. Upon developing the cost reduction targets, the healthcare provider and the analysis provider identify patients within a particular prevention class. As indicated above, this prevention class may be elderly patients that have a higher risk of AFIB. Once this class of patients has been identified, the healthcare provider contacts this group of patients to prompt the group of patients to obtain ECG readings. These ECG readings can come from any one of the ECG acquisition devices 10 shown in FIG. 1. Since the ECG acquisition devices can be one of the wide variety of possible alternatives discussed above, it is much easier for the patients within the prevention class to obtain ECG data as compared to traveling to a health clinic.

Once the ECG data is obtained from the patients in step 154, the ECG data is transmitted to the remote analysis server in step 156 and analyzed in step 158 to determine whether abnormalities, such as arrhythmia are present. The steps are similar to those previously discussed in the method described in FIG. 2. If abnormalities are not detected in step 160, the patient is informed in step 162. However, if abnormalities are detected in step 160, the method moves to step 164 and the patient is informed and the patient is referred to the healthcare provider. Since the patient is already associated with the healthcare provided, the healthcare provider can then contact the patient and schedule additional medical testing and procedures as desired.

Since the patient was identified in step 154 and urged to have an ECG reading taken in step 154, if an abnormality is detected in step 160, it is a patient that would not otherwise have been tested but for the method of FIG. 5. Thus, early detection is a benefit of the method in FIG. 5. In step 166, the analysis provider calculates cost savings based upon the identification of patients at early stages. The calculated cost savings and metrics identified in step 166 are quantified financially and the analysis provider is allocated a percentage of the cost savings. In this manner, the analysis provider is rewarded financially with the cost savings associated with early detection in a patient population that may otherwise not have been tested. As a result of the method shown and described in FIG. 5, early detection for the identified population aids in a healthier population and reduces the overall costs of treatment of the patients. The cost savings is shared with the analysis provider to incentivize the analysis provider to continue to develop algorithms and provide the remote analysis server.

In the system and method shown in the drawing Figures, a patient or other type of person uploads ECG data to the cloud for analysis by the remote analysis server 18 can elect to have the ECG data de-identified such that the ECG data can become part of a larger database of ECG information from patients that can be used for research purposes. As discussed previously, the ECG data acquired by the acquisition device 10 is typically uploaded to the cloud 12 and downloaded by the remote analysis server 18 for analysis and detection of arrhythmias. If arrhythmias are detected, the patient informational and ECG data is relayed to healthcare providers such that the healthcare provider can contact the patient to schedule additional testing and possibly a patient visit.

In the embodiment described in which the health website 28 is part of a large institution, such as the Mayo Clinic, Cleveland Clinic or other large healthcare provider, the large institution may be uploading a large number of ECGs on a daily basis. If each ECG undergoes a de-identification process, the ECG data could be stored and analyzed for research purposes. In the case of a large healthcare institution, the patient identification information can be encrypted such that only when the encryption key is present would the patient's identification information be available. In this manner, the ECG data from a large number of patients can be analyzed for research purposes while the patient information can be retrieved utilizing the encryption key.

In embodiments in which this information is de-identified, a copy of the ECG records could be provided to a database at the remote analysis server 18 without any patient information. This information could then be accessed by other healthcare providers, research institutions or other interested parties without the fear of any patient identification.

As the healthcare provider continues to treat the patient, the de-identified ECG data could be linked with de-identified EMR data, which includes treatment information and outcome data. This additional information would have value and could be sold to drug companies and researchers. In each case, both the ECG data and EMR data would be de-identified to prevent any patient information from being shared with the entities accessing the data.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method for analyzing ECG data obtained from patients, the method comprising:
   obtaining ECG data and patient identification information from the patient utilizing an acquisitions device at a location;
   transmitting the obtained ECG data to an analysis server operated by an analysis provider and located remote from the location;
   obtaining a review quality selection from the patient;
   obtaining a response time selection from the patient;
   analyzing the obtained ECG data utilizing one of a plurality of processing algorithm resident on the analysis server to identify abnormalities in the obtained ECG data, wherein the ECG data is analyzed based on the obtained quality selection and response time selection from the patient;
   informing the patient upon a failure to detect an abnormality in the ECC data;
   referring the patient identification information, ECG data and identified abnormalities to a healthcare provider; and
   providing a referral fee to the analysis provider from the healthcare provider.

2. The method of claim 1 wherein the ECG data and the patient identification information are obtained by one of a plurality of different types of acquisition devices and transmitted to the analysis server over the internet.

3. The method of claim 2 wherein the acquisition device is provided independent of the analysis provider.

4. The method of claim 2 further comprising the step of transmitting identification information for the acquisition device with the ECG data, wherein the identification information indicates a type of the acquisition device.

5. The method of claim 4 wherein the analysis server includes the plurality of stored processing algorithm, wherein one of the plurality of stored processing algorithms is selected based on the type of acquisition device.

6. The method of claim 2 further comprising the step of transmitting acquisition parameters of the acquisition device with the ECG data.

7. The method of claim 6 wherein the analysis server includes the plurality of stored processing algorithm, wherein one of the plurality of stored processing algorithms is selected based on the acquisition parameters.

8. The method of claim 1 wherein the abnormality is arrhythmia.

9. The method of claim 1 wherein the patient identification information includes healthcare provider information for the patient.

10. The method of claim 1 further comprising the steps of:
    providing a web site for the healthcare provider; and
    creating an ECG module within the website to obtain the ECG data from the patient.

11. The method of claim 1 further comprising the step of providing a cost of service to the patient based on the review quality selection and the response time selection.

12. The method of claim 1 wherein one of the review quality selections included human over-reading.

13. The method of claim 1 further comprising the step of obtaining a analysis type selection from the patient.

14. A method for improving healthcare for patients served by a healthcare provider, the method comprising:
    identifying a subset of patients within a prevention class;
    obtaining ECG data and patient identification information from each of the patients in the subset;
    transmitting the obtained ECG data to an analysis server operated by an analysis provider;
    analyzing the obtained ECG data utilizing one of a plurality of processing algorithms resident on the analysis server to identify abnormalities in the obtained ECG data;
    informing the patient upon a failure to detect an abnormality in the ECC data;
    referring the patient identification information, ECG data and identified abnormalities to a healthcare provider for treatment upon the identification of the abnormality;
    calculating a cost savings for the subset of patients; and
    allocating a portion of the cost savings to the analysis provider.

15. The method of claim 14 wherein the ECG data is obtained from the patient at an acquisition device at a location and the analysis server is at a location remote from the location.

16. The method of claim 15 wherein the acquisition device is provided independent of the analysis provider.

* * * * *